US007218700B2

(12) United States Patent
Huber et al.

(10) Patent No.: US 7,218,700 B2
(45) Date of Patent: May 15, 2007

(54) SYSTEM FOR FORMING X-RAYS AND METHOD FOR USING SAME

(75) Inventors: William Hullinger Huber, Scotia, NY (US); Colin Richard Wilson, Niskayuna, NY (US); John Scott Price, Niskayuna, NY (US); Peter Michael Edic, Albany, NY (US); Mark Ernest Vermilyea, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/048,158

(22) Filed: Feb. 1, 2005

(65) Prior Publication Data

US 2005/0265520 A1 Dec. 1, 2005

Related U.S. Application Data

(60) Provisional application No. 60/576,147, filed on May 28, 2004.

(51) Int. Cl.
*A61B 6/00* (2006.01)

(52) U.S. Cl. ......................... 378/10; 378/136; 378/137

(58) Field of Classification Search ................ 378/119, 378/121, 124, 134, 136; 313/309–311, 346 R, 313/346 DC, 351, 495
See application file for complete search history.

(56) References Cited

U.S. PATENT DOCUMENTS

| | | | | |
|---|---|---|---|---|
| 4,130,759 | A * | 12/1978 | Haimson | 378/10 |
| 4,182,955 | A | 1/1980 | Davis | 378/113 |
| 5,528,658 | A | 6/1996 | Hell | 378/137 |
| 5,822,394 | A | 10/1998 | Schardt et al. | 378/125 |
| 6,009,141 | A | 12/1999 | Hell et al. | 378/10 |
| 6,259,765 | B1 | 7/2001 | Baptist | 378/136 |
| 6,385,292 | B1 | 5/2002 | Dunham et al. | 378/122 |
| 6,649,914 | B1 | 11/2003 | Moorman et al. | 250/363.06 |
| 6,731,716 | B2 | 5/2004 | Mihara et al. | 378/9 |
| 6,807,248 | B2 | 10/2004 | Mihara et al. | 378/10 |
| 2004/0114721 | A1 * | 6/2004 | Qiu et al. | 378/122 |

FOREIGN PATENT DOCUMENTS

| | | | |
|---|---|---|---|
| DE | 19621066 | A1 | 5/1996 |
| EP | 0024325 | B1 | 9/1983 |
| EP | 0657915 | B1 | 7/1998 |
| WO | WO03/051201 | | 6/2003 |

OTHER PUBLICATIONS

PCT/US2005/012807 dated Nov. 30, 2005, International Filing Date Apr. 14, 2005, International Search Report.

* cited by examiner

*Primary Examiner*—Courtney Thomas
(74) *Attorney, Agent, or Firm*—William E. Powell, III; Curtis B. Brueske

(57) ABSTRACT

A system and method for forming x-rays. One exemplary system includes a target and electron emission subsystem with a plurality of electron sources. Each of the plurality of electron sources is configured to generate a plurality of discrete spots on the target from which x-rays are emitted. Another exemplary system includes a target, an electron emission subsystem with a plurality of electron sources, each of which generates at least one of the plurality of spots on the target, and a transient beam protection subsystem for protecting the electron emission subsystem from transient beam currents, material emissions from the target, and electric field transients.

28 Claims, 8 Drawing Sheets

SYSTEM FOR FORMING X-RAYS AND METHOD FOR USING SAME

CROSS-REFERENCE TO RELATED APPLICATIONS

This application claims the benefit of U.S. Provisional Application No. 60/576,147, filed May 28, 2004, which is incorporated in its entirety herein by reference.

BACKGROUND

The invention relates generally to a system for forming x-rays, and more particularly to a system configured to direct electron beams at a plurality of discrete spots on a target to form x-rays.

X-ray scanning has been used in medical diagnostics, industrial imaging, and security related applications. Commercially available x-ray sources typically utilize conventional thermionic emitters, which are helical coils made of tungsten wire and operated at high temperatures. Each thermionic emitter is configured to emit a beam of electrons to a single focal spot on a target. To obtain a total current of 10 to 20 mA with an electron beam size of 10 $mm^2$, helical coils formed of a metallic wire having a work function of 4.5 eV must be heated to about 2600 K. Due to its robust nature, tungsten wire has been the electron emitter of choice.

There are disadvantages to the use of conventional thermionic filament emitters. Such filament emitters lack a uniform emission profile necessary for proper beam steering and focusing. Further, a higher electron beam current will cause a reduction in the lifetime of such filament emitters. Additionally, such filament emitters require high quiescent power consumption, which leads to the need for larger, more complex cooling architectures, a larger system envelope, and greater cost.

SUMMARY

An exemplary embodiment of the invention provides a system for forming x-rays that includes a target and at least one electron emission subsystem for generating a plurality of spots on the target. The at least one electron emission subsystem includes a plurality of electron sources and each of the plurality of electron sources generates at least one of the plurality of spots on the target. The system also includes a beam focusing subsystem for focusing electron beam emissions from the plurality of electron sources prior to the electron beam emissions striking the target.

Another exemplary embodiment of the invention provides a system for forming x-rays that includes a target, an electron emission subsystem for generating a plurality of spots on the target, and a transient beam protection subsystem for protecting the electron emission subsystem from transient beam currents, material emissions from the target, and electric field transients. The electron emission subsystem includes a plurality of electron sources.

Another exemplary embodiment of the invention provides a system for forming x-rays that includes a target and an electron emission subsystem including a plurality of electron sources. The electron emission subsystem is configured to generate a plurality of discrete spots on the target from which x-rays are emitted. The target is enclosed within a first vacuum chamber and the electron emission subsystem is enclosed within a second vacuum chamber.

Another exemplary embodiment of the invention provides a method for x-ray scanning an object that includes emitting a beam of electrons from an electron source to strike a discrete or swept focal spot on a target for creating x-rays from the discrete or swept focal spot. The method further includes focusing the beam of electrons from the electron source prior to the electron beam emissions striking the target and detecting the x-rays created from the discrete or swept focal spots.

These and other advantages and features will be more readily understood from the following detailed description of preferred embodiments of the invention that is provided in connection with the accompanying drawings.

Figure 1:
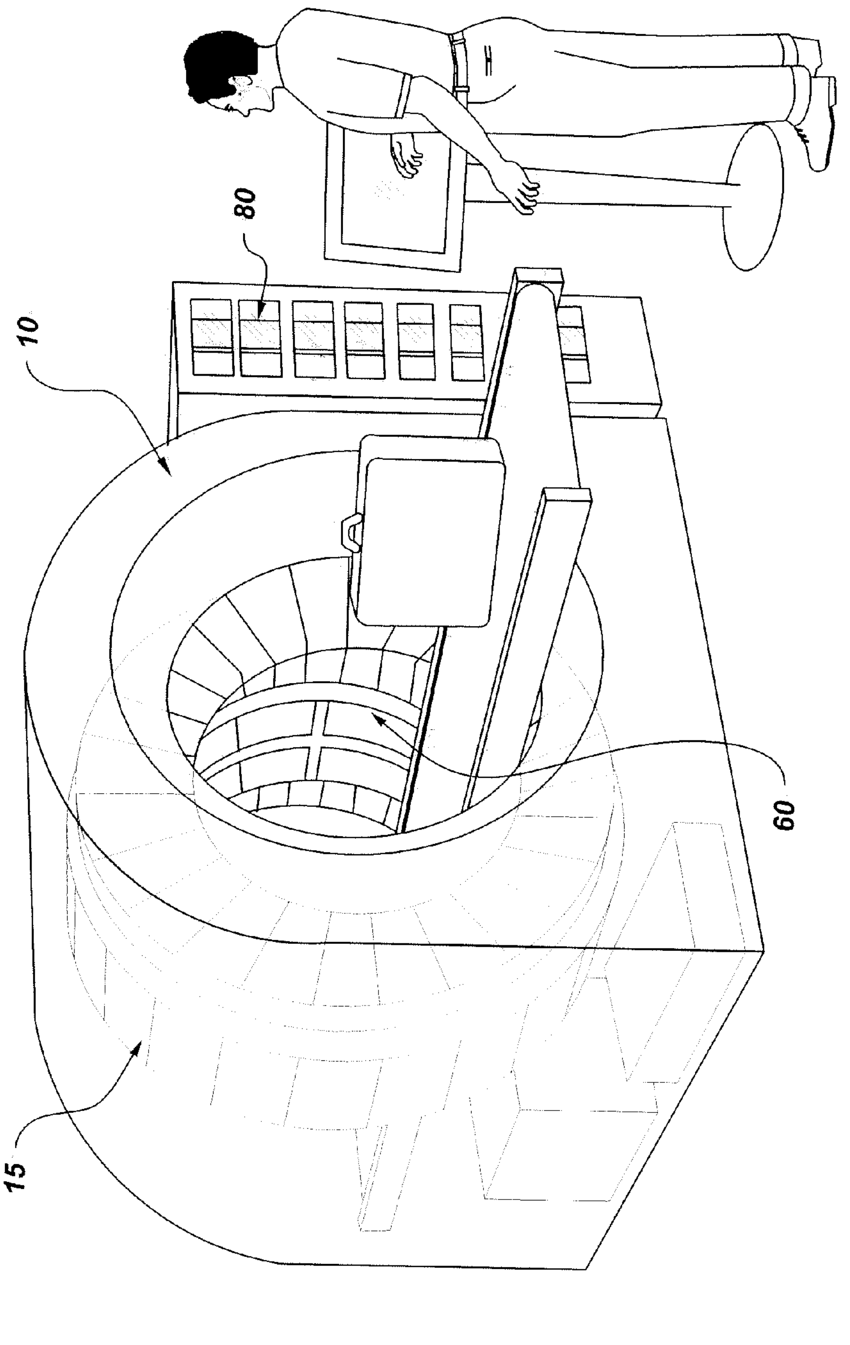
FIG. 1 is a schematic view of an x-ray system constructed in accordance with an exemplary embodiment of the invention.

FIG. **8*a* is a perspective view of an alternative source for use in the x-ray system of FIG. 1**.

Figure 8A:
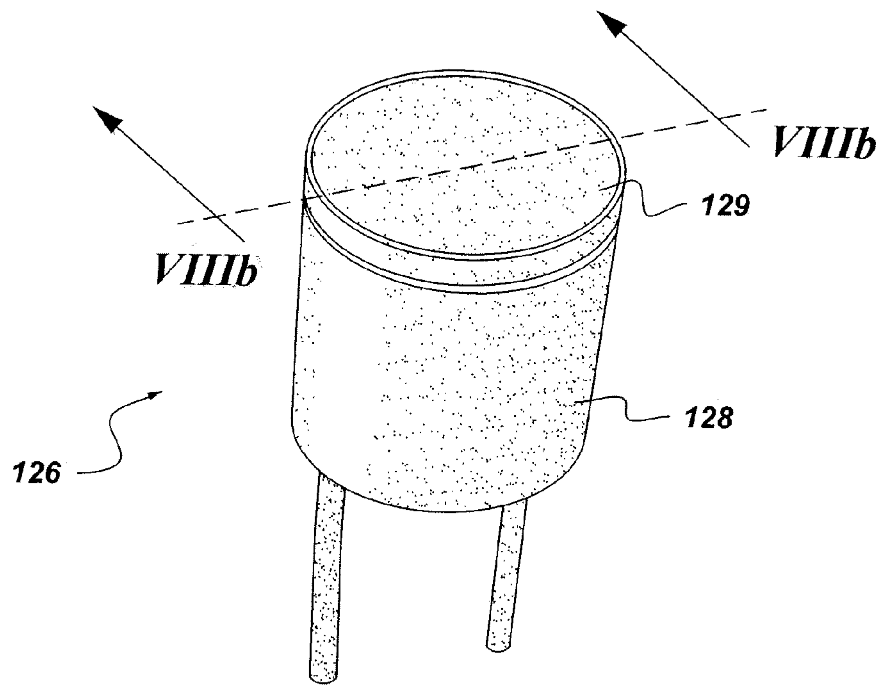

FIG. **8*b* is a cross-sectional view of the electron source of FIG. 8*a*** taken along line VIIIa—VIIIa.

Figure 9:
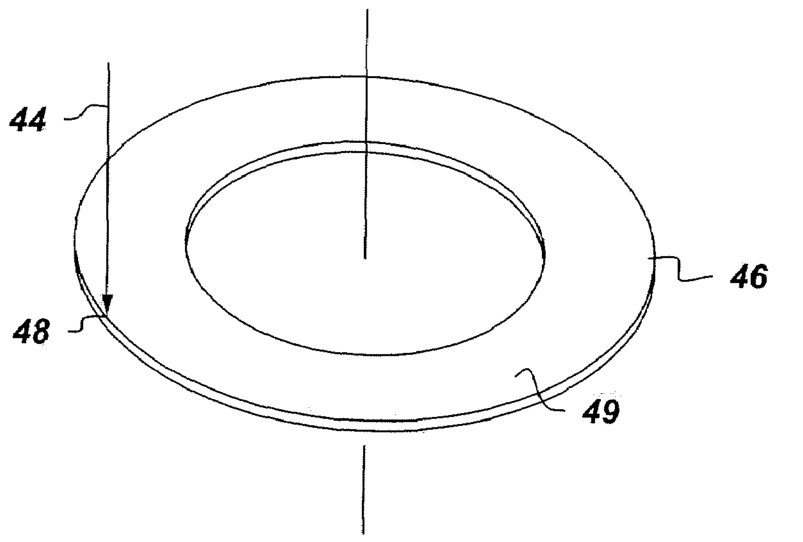

FIG. 9 is a perspective view of a target constructed in accordance with another exemplary embodiment of the invention.

Figure 10:
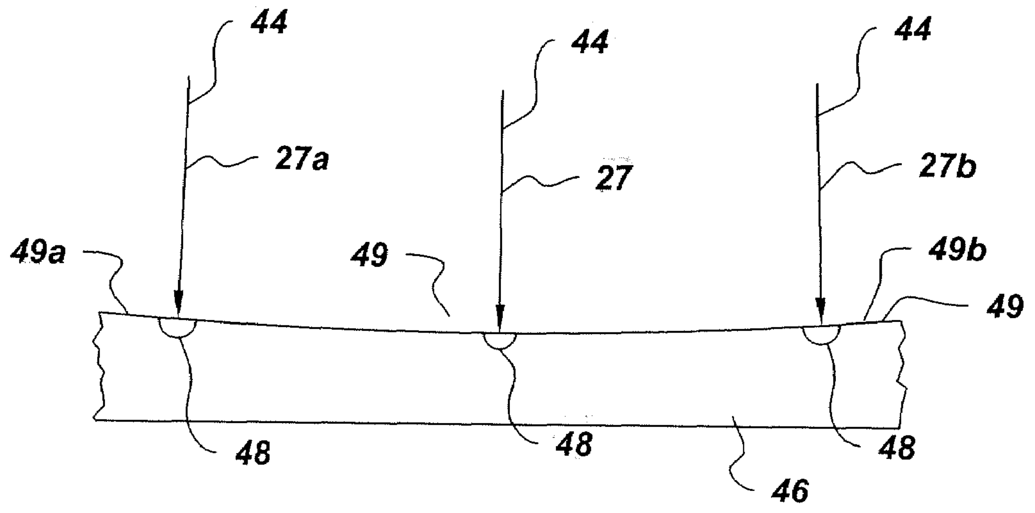

FIG. 10 is a side view of a portion of the target of FIG. 9.

Figure 11:
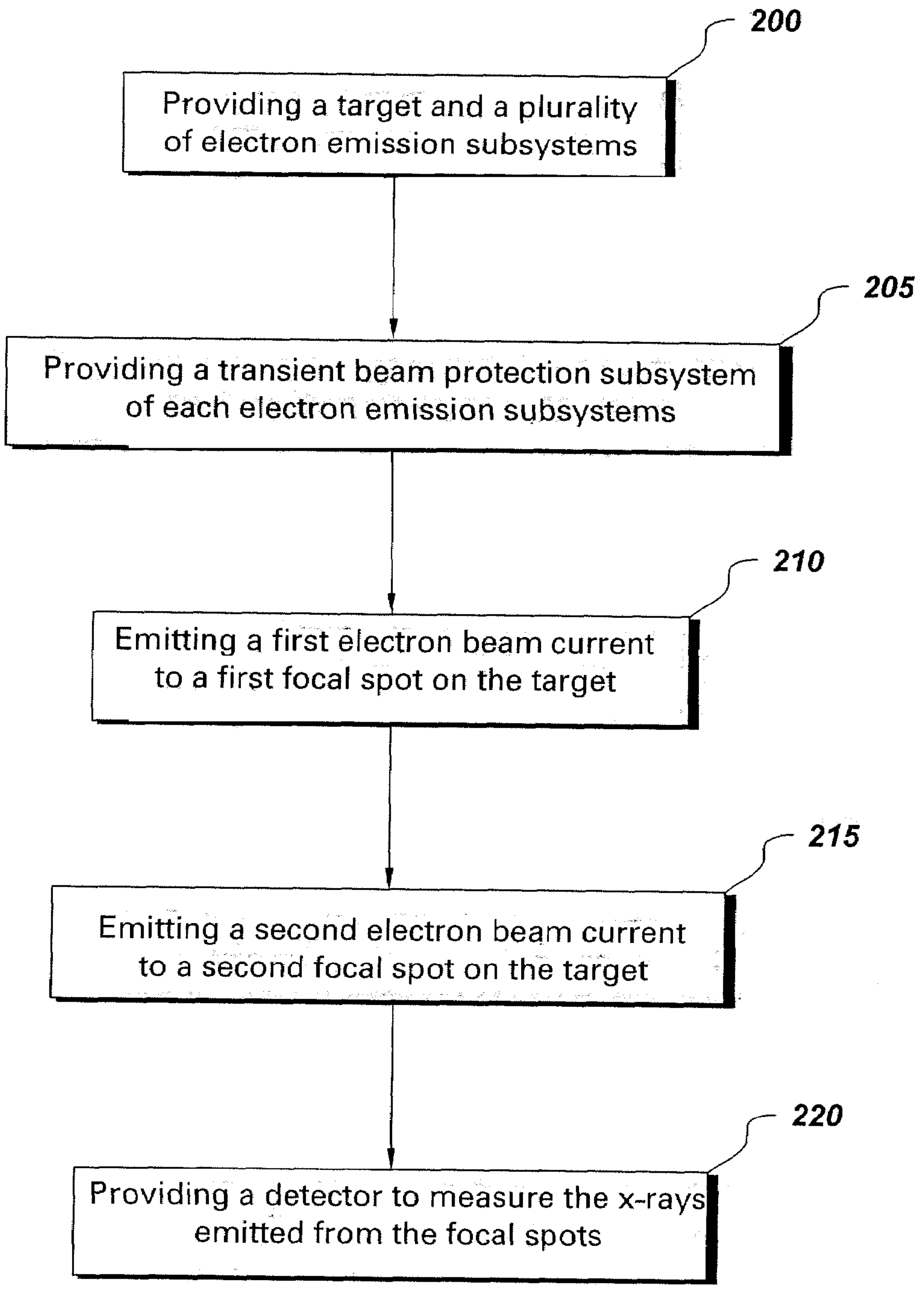

FIG. 11 illustrates process steps for obtaining x-rays of a subject in accordance with another exemplary embodiment of the invention.

DETAILED DESCRIPTION OF PREFERRED EMBODIMENTS

Figure 2:
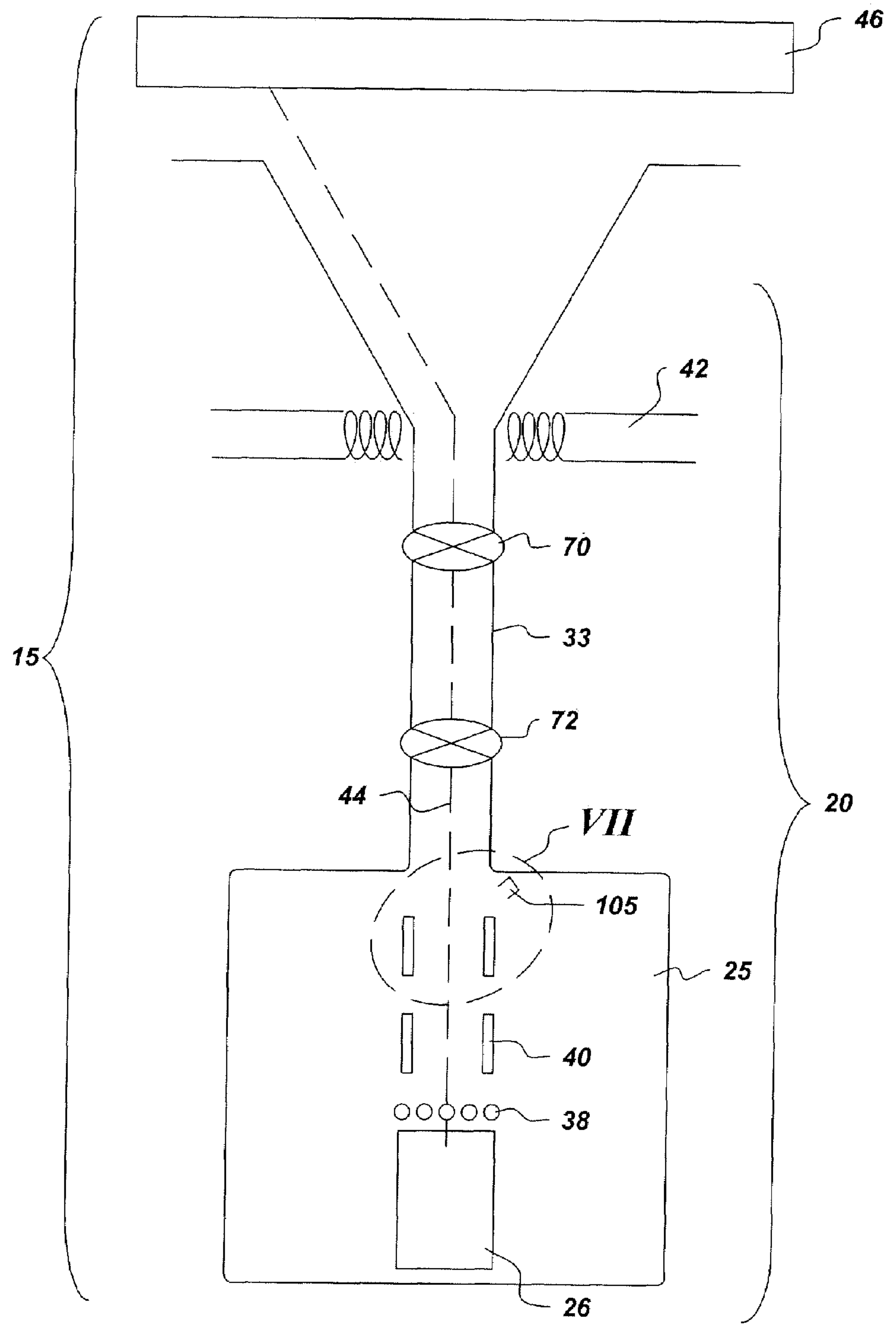
FIG. 2 is a schematic view of an exemplary embodiment of an x-ray generation subsystem for use in the x-ray system of FIG. 1.
Figure 6:
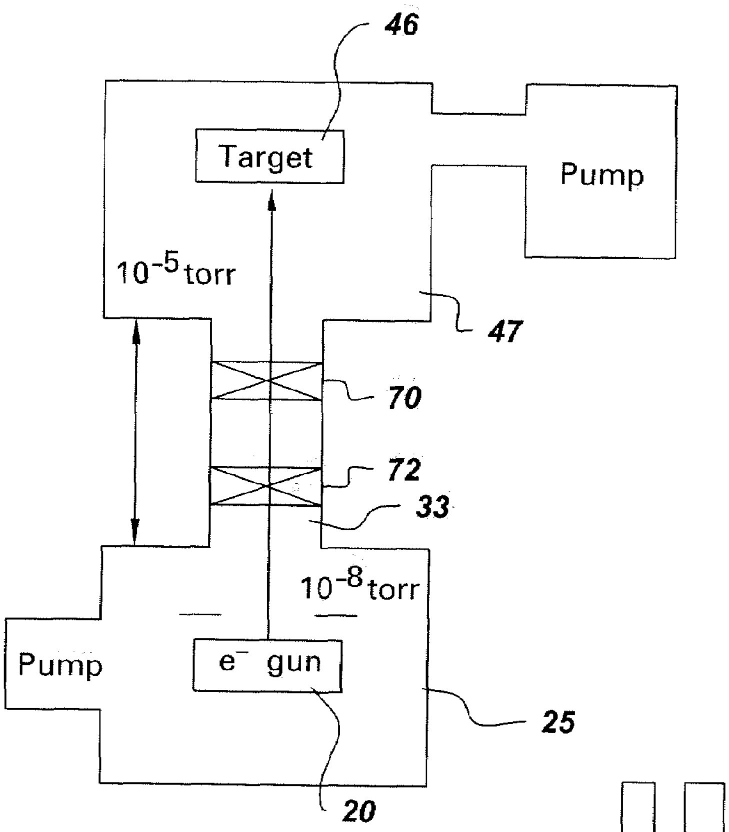
FIG. 6 is a schematic representation of the source and target vacuums of FIG. 5.

With reference to FIGS. 1 and 2, first will be described an x-ray system 10. The x-ray system 10 includes an x-ray generation subsystem 15 including a target 46 (FIG. 2), a detector 60, and an electronic computing subsystem 80. A portion of the x-ray generation subsystem 15, which may include a steerable electron emission subsystem 20, may be encompassed in a first vacuum vessel 25, while the target 46 may be encompassed within a second vacuum vessel or target chamber 47 (FIG. 6). The x-ray system 10 may be configured to accommodate a high throughput of articles, for example, screening of upwards of one thousand individual pieces of luggage within a one hour time period, with a high detection rate and a tolerable number of false positives. Conversely, the x-ray system 10 may be configured to accommodate the scanning of organic subjects, such as humans, for medical diagnostic purposes. Alternatively, the x-ray system 10 may be configured to perform industrial non-destructive testing. The electron emission subsystem 20 and the target 46 may be stationary relative to the detector 60, which may be stationary or rotating, or the electron emission subsystem 20 and the target 46 may rotate relative to the detector 60, which may be stationary or rotating.

With specific reference to FIGS. 2 and 4, next will be described an exemplary embodiment of the x-ray generation subsystem 15 including the electron emission subsystem 20. It should be appreciated that multiple electron emission subsystems 20 may be arranged around the target 46. The electron emission subsystem 20 includes an electron source 26. Each electron beam generated within the electron emission subsystem 20 is steerable. The electron source 26 is positioned within the electron emission subsystem 20 such that the electron emission subsystem 20 serves as a transient beam protection subsystem protecting the electron source 26 from transient voltages and/or currents. In addition, the electron emission subsystem 20 protects the electron source 26 from sputter damage gasses in the target chamber 47 (FIG. 6). Specifically, a channel 33 extends between the target 46 and the electron source 26 to alleviate the deleterious effects of transient beam currents and material emissions striking at or near the electron source 26. The transient beam protection subsystem functions more efficiently if the differential between the voltage potential of the target 46 is significantly higher than the voltage potential of the electron source 26 and its surrounding environs. Such a transient beam protection subsystem serves to sink current from one or more electron sources if the potential of the anode or target 46 drops and to provide protection for one or more electron sources during transient beam emissions.

It should be appreciated that a different architecture may be utilized to effect the emission of electron beams to more than one focal spot on the target 46. Instead of utilizing a steerable electron emission subsystem as described with reference to the x-ray generation subsystem 15, a dedicated emitter design architecture may be used. For example, and with specific reference to FIG. 3, an x-ray generation subsystem 115 may be used, which includes an electron emission subsystem 120 having an emitter array 122. The emitter array 122 includes a plurality of electron sources 26, each positioned within an alcove 29 and each being configured to emit a beam 44 of electrons to a discrete focal spot 48 on the target 46. The transient beam protection subsystem for the FIG. 3 embodiment may include the combination of the channel 33, and the alcoves 29. The transient beam protection subsystem may also include guard electrodes (not shown) as a further protection mechanism. Furthermore, such a transient beam protection subsystem serves to (a) sink current from one or more electron sources if the potential of the target 46 drops and (b) provide protection for one or more electron sources during transient beam emissions.

It also should be appreciated that several types of electron sources, or emitters, may be utilized. Examples of suitable electron emitters include tungsten filament, tungsten plate, field emitter, thermal field emitter, dispenser cathode, thermionic cathode, photo-emitter, and ferroelectric cathode, provided the electron emitters are configured to emit an electron beam at multiple discrete focal spots on a target.

Figure 7:
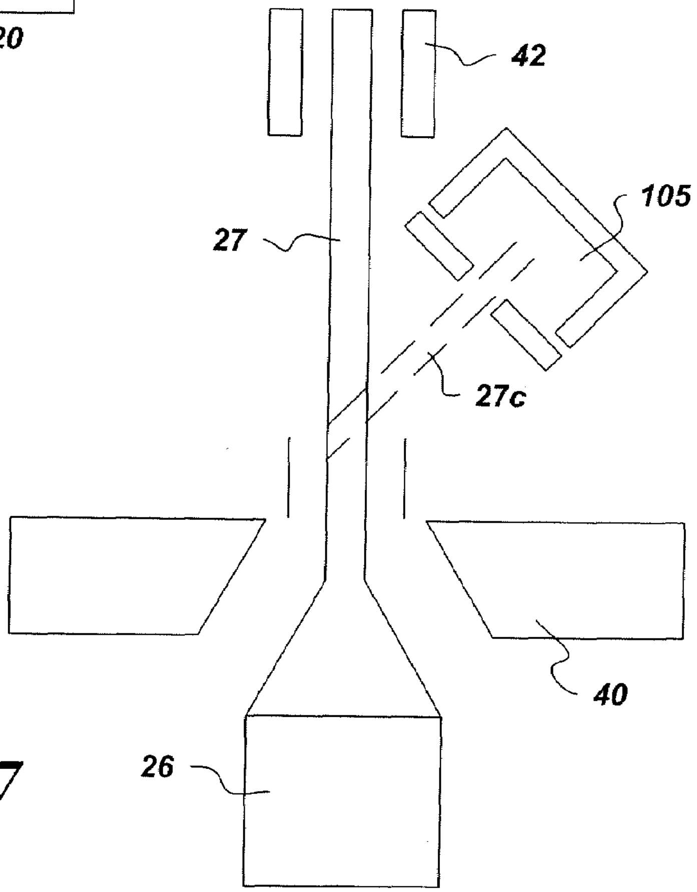
FIG. 7 is an expanded view of the beam dump mechanism within circle VII of FIG. 2.

The x-ray generation subsystem 15 includes a beam focusing subsystem 40, a beam deflection subsystem 42, and a pinching electrode for selectively inhibiting or permitting electron beams from the electron source 26 to be emitted toward the target 46. One such mechanism is a pinch-off plate or beam grid, which is configured to pinch off electron beams 44 when activated. Another such mechanism is a conducting gate 32 (FIG. 4), which is configured to facilitate electron beam 44 generation when activated. Yet another mechanism is a beam dump 105 (FIGS. 2, 7). The beam dump 105, when activated, diverts the electron beams 44 away from an undeflected path 27 toward the target 46 (FIGS. 2, 6, 7) to a deflected path 27*c* into the container.

The beam focusing subsystem 40 serves to form and focus a beam 44 of electrons into a pathway 27 (FIG. 5) toward the target 46. The beam focusing subsystem 40 may include an electrostatic focusing component, such as, for example, a plurality of focusing plates each biased at a different potential, or a magnetic focusing component, such as, for example, a suitable combination of focusing solenoids, deflecting dipoles and beam-shaping quadrupole electromagnets. Electromagnets that produce higher order moments (6-pole, 8-pole, etc.) can be used to improve beam quality or to counter effects of edge-focusing that may occur due to a particular choice or design of elements in subsystem 40.

The beam deflection subsystem 42 serves to steer or deflect the electrons from the pathway 27 onto deflected pathways 27*a*, 27*b* (FIG. 5) toward numerous discrete focal spots 48 on the target 46 (FIG. 10). The ability to steer electron beams to more than one focal spot 48 on the target 46 is significant in that it facilitates the use of a reduced number of electron emitters relative to the required number of x-ray focal spots. The electron source 26 may be a low current-density electron source. Optics, such as the beam focusing subsystem 40, is used to form high current-density beams 44 at the target 46 from a low current-density electron source. Each discrete electron beam 44 strikes the focal spots 48 on the target 46, creating x-ray beams 50 (FIG. 3) which will be used to scan a subject, be it inorganic or organic. It should be appreciated that a beam deflection subsystem 42 may be unnecessary for an arrangement of electron sources such as the x-ray generation subsystem 115 having an emitter array 122 illustrated in FIG. 3, although a beam focusing subsystem 40 may still be employed. Since a plurality of electron sources 26 would be located adjacent to one another, steering the electron beams 44 from each electron source 26 likely would not be needed to produce electron beam strikes at a plurality of focal spots 48 on the target 46.

The beam deflection subsystem 42 may be electrostatically-based, magnetically-based, or a combination of the two. For example, the beam deflection subsystem 42 may include an electrostatic steering mechanism that has one or more free standing electrically conducting plates that may be positioned within the channel 33. As beam currents 44 of electrons are emitted from the electron source 26, the plates can be charged to a fairly high negative potential with respect to ground. The plates may be formed of an electrically conductive material, or be formed of an insulating material and coated with an electrically conductive coating. The beam deflection subsystem 42 may include a magnetic steering mechanism with a magnetic core for correcting magnetic fields that have other higher-moment fields, such as, for example, hexapoles, so that the focal spot 48 (FIGS. 3, 10) shape is maintained over a wide set of deflection angles. Alternatively, the magnetic steering mechanism may have no magnetic core. Examples of suitable magnetic steering mechanisms include one or more coils, a coil-shaped electromagnet, and a fast switching magnetic-field-producing magnet, each of which being capable of producing magnetic fields with substantial quadrupole moments as well as dipole moments.

Figure 5:
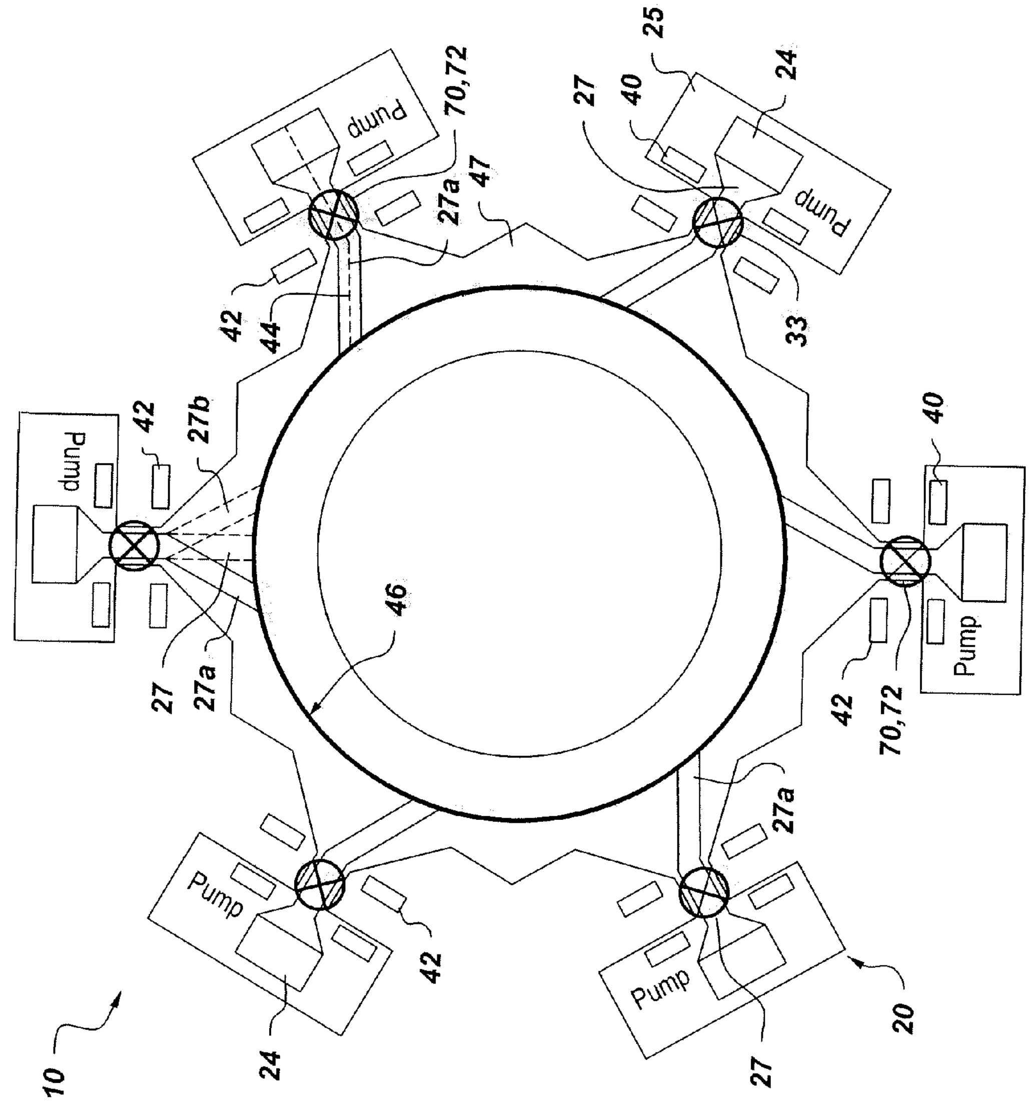
FIG. 5 is a schematic view, of multiple steerable electron emission subsystems within the x-ray system of FIG. 1.

As described above, each electron emission subsystem 20 may be encompassed in a first vacuum vessel 25, while the target 46 may be encompassed within a second vacuum vessel 47 (FIGS. 5, 6). Each of the first vacuum vessels 25 is separated from the second vacuum vessel 47 via a channel

33. The differential pressures of each of the vacuum vessels 25, 47 are maintainable through the use of differential pumping through a narrow diameter pipe. As an exemplary embodiment, two gate valves 70, 72 connect each first vacuum vessel 25 with the second vacuum vessel 47 through the channels 33. Through this arrangement, if replacement of any single electron source 26 is required, the gate valve 70 may be kept in a closed state while the gate valve 72 is opened to allow removal of the electron source 26 from the vacuum vessel 25. Alternatively, a single gate valve may be used to separate the two vacuum vessels 25, 47.

Figure 3:
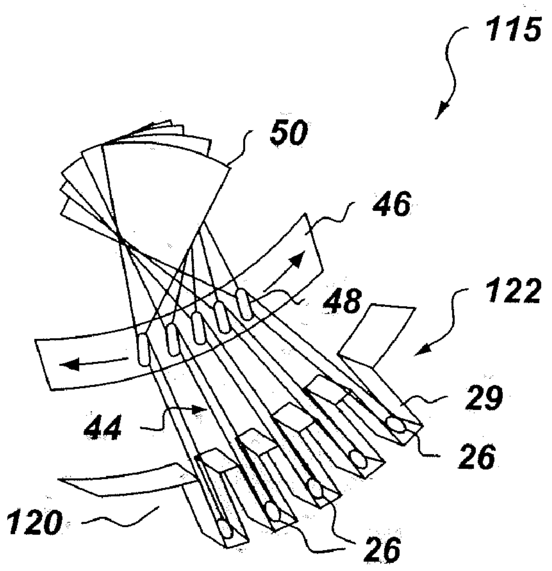
FIG. 3 is a schematic view of an exemplary embodiment of an electron source array for use in the x-ray system of FIG. 1.
Figure 4:
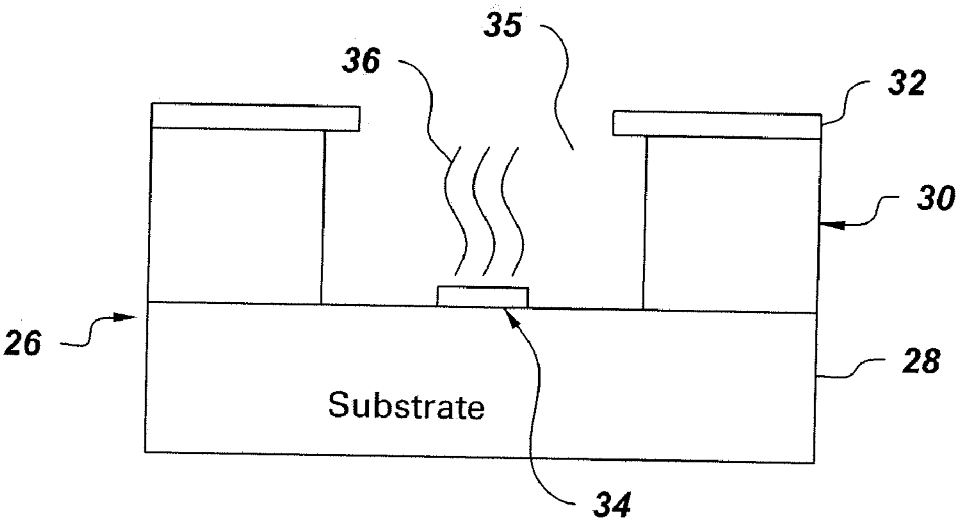
FIG. 4 is a side view of an electron source for use in the x-ray system of FIG. 1.

Referring now to FIG. 4, next will be described an exemplary embodiment of the electron source 26 of FIGS. 2 and 3. The electron source 26 illustrated in FIG. 4 includes a base or substrate 28 and carbon nanotubes 36. The carbon nanotubes 36 are positioned on a catalyst pad 34, which is itself located on a surface of the substrate 28. The substrate 28 may be formed of silicon or another like material. A dielectric spacer 30 is positioned over the substrate 28. A well 35 is etched in the dielectric spacer 30, and the catalyst pad 34 is positioned therein. A conducting gate 32, positioned over the spacer 30, serves to generate high electric fields in the vicinity of the tips of the carbon nanotubes 36, which promotes electron emissions within electron source 26. The carbon nanotubes 36 may be grown selectively on the catalyst pad 34 through the use of chemical vapor deposition. The inherently high aspect ratio makes them particularly well suited for field emission.

Figure 8B:
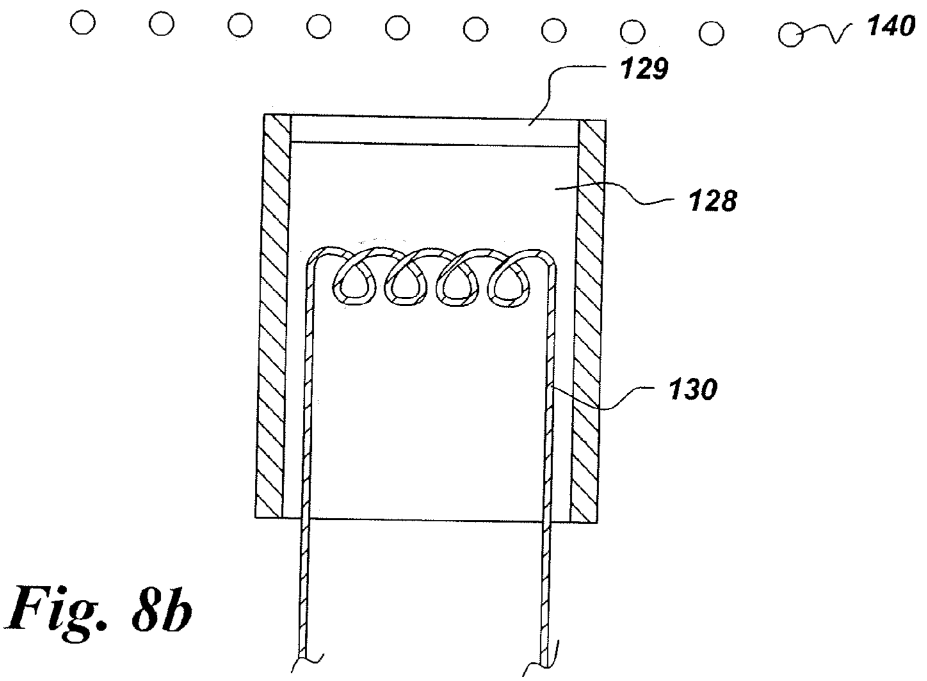

Alternatively, and with specific reference to FIGS. 8*a*, 8*b*, a dispenser cathode 126 may be utilized as an electron source. The dispenser cathode 126 may include a container 128 with a porous tungsten plug 129. A coil 130, preferably formed of tungsten, is positioned within the container 128 and surrounded by an oxide-based solution, such as, for example, barium oxide, calcium oxide, or tin oxide. A gridding mechanism 140 (FIG. 8*b*) may be placed between the dispenser cathode 126 and the target 46 (FIGS. 2, 5, 6) to permit or inhibit electron emissions from the dispenser cathode 126 from striking the target 46. The oxide materials coat the tungsten plug 129, thereby lowering the work function for the dispenser cathode 126. One advantage of using a dispenser cathode 126 is that the lowered work function requires that the tungsten coil 130 only needs to be heated up to 1300° C., instead of the 2500° C. required for uncoated tungsten thermionic emitters. A further advantage is the low cost of off-the-shelf dispenser cathodes 126. When the oxide materials have evaporated away, the dispenser cathode 126 can be discarded and replaced with another.

Next will be described the x-ray system 10 as illustrated in FIG. 5. A plurality of electron emission subsystems 20 is arrayed around a target 46. Each of the electron emission subsystems 20 is within a first vacuum vessel 25, while the target 46 is within a second vacuum vessel 47. Each of the vacuum vessels 25, 47 are pumped so as to obtain a differential pressure between each of the first vacuum vessels 25 and the second vacuum vessel 47. Each of the first vacuum vessels 25 is connectable with the second vacuum vessel 47 through a channel 33. The differential pressure between the first vacuum vessels 25 and the second vacuum vessel 47 is maintained through the use of differential pumping. While six discrete electron emission subsystems 20 are illustrated each within a separate first vacuum vessel 25, it should be appreciated that any number of electron emission subsystems 20 may be utilized. The beam deflection subsystem 42 steers the electron beams 44 (FIGS. 2, 3) from the pathway 27 to a deflected pathway 27*a*, 27*b* to strike the target 46 at an alternative discrete focal spot 48 (FIG. 3).

With specific reference to FIGS. 9, 10, next will be described an exemplary embodiment of the target 46. The target 46, as illustrated in FIGS. 9 and 10 includes target planes 49, 49*a*, and 49*b*. Target planes 49*a* and 49*b* are at an angle to target plane 49. An undeflected electron beam 44 is intended to follow pathway, 27 to strike the target 46 at a focal spot 48 along target plane 49. Alternatively, a deflected electron beam 44 is intended to follow the deflected pathway 27*a* or 27*b* to strike the target 46 at a focal spot 48 along target plane 49*a* or 49*b*. The target planes 49, 49*a*, 49*b* may be curved surfaces or they may be flat surfaces at an angle relative to one another. The angle of incidence of target planes 49*a* and 49*b* is chosen such that the deflected electron beams 44 strike the focal spots 48 along the target planes 49*a*, 49*b* at the same angle as the undeflected electron beam 44 strikes the focal spot 48 along the target plane 49. In this manner, the beam deflection subsystem 42 (FIGS. 2, 5) can deflect electron beams 44 to strike a plurality of focal spots 48 along the target 46 such that the similar x-ray energy spectrum is exhibited from strikes along all the target planes 49, 49*a*, 49*b* and such that each strike produces a similar angle of emission of x-ray beams 50 (FIGS. 2, 3).

Next, with reference to FIG. 1, will be described the detector 60 and the electronic computing subsystem 80. The detector 60 may include a detector ring positioned adjacent to the x-ray generation subsystem 15. The detector ring may be offset from the x-ray generation subsystem 15. It should be appreciated, however, that "adjacent to" should be interpreted in this context to mean the detector ring is offset from, contiguous with, concentric with, coupled with, abutting, or otherwise in approximation with the x-ray generation subsystem 15. The detector ring may include a plurality of discrete detector modules that may be in linear, multi-slice, or area detector arrangements. Moreover, energy-integration, photon-counting, or energy-discriminating detectors may be utilized, comprising scintillation or direct conversion devices. An exemplary embodiment of the detector module includes a detector cell having a pitch of, for example, two millimeters by two millimeters, providing an isotropic resolution on the order of one millimeter in each spatial dimension. Another exemplary embodiment of the detector module includes a detector cell having a pitch of one millimeter by one millimeter.

The electronic computing subsystem 80 is linked to the detector 60. The electronic computing subsystem 80 functions to reconstruct the data received from the detector 60, segment the data, and perform automated detection and/or classification. One embodiment of the electronic computing subsystem 80 is described in U.S. patent application Ser. No. 10/743,195, filed Dec. 22, 2003, which is incorporated in its entirety by reference herein.

There are several advantages to the aforementioned arrangement of features in the x-ray system 10. By utilizing steerable electron sources, such as the electron sources in the x-ray generation subsystem 15, and the target planes 49, 49*a*, 49*b*, the range of electron beams 44 (FIG. 2) from each electron source 26 is expanded with a minimal loss of resolution. The expanded range of electron beams 44 may translate into some redundancy, wherein some of the electron beams 44 from one electron source 26 may overlap others of the electron beams 44 from adjacent electron sources 26. Further, the expanded range of electron beams 44 may translate into a longer working life of the x-ray system 10 between maintenance since the increased redundancy may allow the x-ray system 10 to be used with a larger number of inoperable electron emission subsystems 20.

Another advantage of the x-ray system 10 is that the arrangement of the transient beam protection subsystem inhibits transient vacuum arcs, vacuum discharges, or spits from the target 46 striking at or near the electron sources 26. The channel 33 provides a narrow pathway through which a spit will unlikely be able to traverse all the way back to the electron sources 26. Further, the alcoves 29 can minimize any sputter damage to the electron sources 26. Additionally, the transient beam protection subsystem can sink current from the electron source 26 if the electric field within the x-ray generation subsystem 15 collapses due to discharges.

Furthermore, using the architecture of the x-ray system 10 reduces the concern about the power dissipation of the electron sources 26, since the amount of power that is used is considerably less than in a comparable x-ray system utilizing thermionic electron emitters. In a conventional x-ray system, the focal spot positions are positioned adjacent to one another, providing little space in which to place focusing mechanisms. In a dedicated emitter design (FIG. 3) of x-ray generation subsystem 15, an electron source is required for each x-ray spot 48. The emitters are positioned so close to each other that incorporating beam optics to deflect the beam would be difficult to achieve. Thus, to generate, for example, one-thousand x-ray spots 48, one-thousand electron emitters would be necessary. As thermionic emitters typically require approximately 10 watts of power to emit electrons, the overall power requirement is difficult to accommodate. The use of the beam focusing subsystem 40 allows for lower-density electron sources to be used, and the use of a beam deflection subsystem 42 permits multiple x-ray spots from a single electron source, and the use of alternative electron emitters (dispenser cathodes, field emission devices, for example) reduces quiescent power consumption, all of which reduce the overall power consumption.

With specific reference to FIG. 11, next will be described a method for x-ray scanning an object. At Step 200, a plurality of electron emission subsystems is provided adjacent to a target. At Step 205, a transient beam protection subsystem is positioned in the vicinity of each electron emission subsystem arranged about the target. For example, each electron emission subsystem 20, 120 may be segregated from the target 46 through the use of the transient beam protection subsystem, including one or more of channel 33, the alcove 29, or guard electrodes (not shown). The transient beam protection subsystem is designed to provide protection to the electron sources 26 against transient beam currents/voltages, material emissions from the target 46, and collapse of the electric field.

At Step 210, a first electron beam current is emitted from an electron emission subsystem to a first focal spot 48 on the target 46. At Step 215, a second electron beam current is emitted from an electron emission subsystem to a second focal spot 48 on the target. For electron emission subsystems 20, a single electron source 26 transmits both of the electron beam currents and one of the electron beam currents is subjected to deflection. For electron emission subsystems 120, which each incorporate an array of electron sources 26, no deflection of the electron beam currents is necessary, since each electron source is offset from the others. It should be appreciated that there may be numerous times that a current is emitted to a focal spot 48 on the target 46, and that there may be a loop executed N number of times, depending on the number of focal spots 48 desired.

Finally, at Step 220, a detector, such as the detector 60, is provided to measure the x-rays emitted from the focal spots on the target.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while field emitters and dispenser cathodes have been generally described, it should be appreciated that various embodiments of the invention may incorporate field emitters and/or dispenser cathodes that are anode grounded, cathode grounded, or multi-polar. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A system for forming x-rays, comprising:

a target;

at least one electron emission subsystem for generating a plurality of spots on said target, wherein said at least one electron emission subsystem comprises a plurality of electron sources and wherein each of said plurality of electron sources generates at least one of said plurality of spots on said target;

a beam focusing subsystem for focusing electron beam emissions from said plurality of electron sources prior to said electron beam emissions striking said target, and thereby forming x-rays; and a transient beam protection subsystem comprising at least one structure configured to perform at least one of:

sink current from each of said plurality of electron sources if a potential of the target drops; and provide protection for each of said plurality of electron sources during transient beam emissions.

2. The system of claim 1, wherein said beam focusing subsystem comprises an electrostatic focusing component.

3. The system of claim 1, wherein said beam focusing subsystem comprises a magnetic focusing component.

4. The system of claim 1, wherein each of said plurality of electron sources comprises one from the group consisting of field emitter, thermal field emitter, tungsten wire, coated tungsten wire, tungsten plate, photo-emissive surface, dispenser cathode, thermionic cathode, photo-emitter, and ferroelectric cathode.

5. The system of claim 1, further comprising a pinching electrode configured to selectively permit and inhibit generation of said plurality of spots on said target.

6. A system for forming x-rays, comprising:

a target;

an electron emission subsystem for generating a plurality of spots on said target, thereby forming x-rays, wherein said electron emission subsystem comprises a plurality of electron sources; and a transient beam protection subsystem for protecting said electron emission subsystem from transient beam currents, material emissions from said target, and electric field transients, wherein said transient beam protection subsystem comprises at least one structure configured to perform at least one of:

sink current from each of said plurality of electron sources if a potential of the target drops; and provide protection for each of said plurality of electron sources during transient beam emissions.

7. The system of claim 6, wherein each of said plurality of electron sources comprises one from the group consisting of field emitter, thermal field emitter, tungsten wire, coated tungsten wire, tungsten plate, photo-emissive surface, dispenser cathode, thermionic cathode, photo-emitter, and ferroelectric cathode.

8. The system of claim 6, wherein each of said plurality of electron sources generates at least one of said plurality of spots on said target.

9. The system of claim 6, wherein said transient beam protection subsystem comprises positioning each of said plurality of electron sources within an alcove.

10. The system of claim 6, wherein said transient beam protection subsystem comprises a channel extending between each of said plurality of electron sources and said target.

11. A system for forming x-rays, comprising:

a target; and an electron emission subsystem comprising a plurality of electron sources, said electron emission subsystem being configured to generate a plurality of discrete spots on said target from which x-rays are emitted;

wherein said target is enclosed within a first vacuum vessel and said electron emission subsystem is enclosed within a second vacuum vessel.

12. The system of claim 11, wherein said first and second vacuum vessels are each pumped.

13. The system of claim 11, wherein said first and second pumped vacuum vessels are connected with a channel used to transport electron beams from said second vessel to said first vessel.

14. The system of claim 11, wherein said second pumped vacuum vessel is separable from said first pumped vacuum vessel with one or more gate valves.

15. The system of claim 11, wherein each said electron source is positioned within an alcove configured to inhibit damage to said electron source from a deflection of a beam of electrons from the target toward said electron source.

16. The system of claim 11, wherein each of said electron sources comprises one from the group consisting of field emitter, thermal field emitter, tungsten wire, coated tungsten wire, tungsten plate, photo-emissive surface, dispenser cathode, thermionic cathode, photo-emitter, and ferroelectric cathode.

17. The system of claim 11, further comprising at least one detector.

18. The system of claim 17, wherein each said electron source and said target are stationary relative to said detector, which either rotates or is stationary.

19. The system of claim 17, wherein each said electron source and said target rotate relative to said detector, which either rotates or is stationary.

20. The system of claim 11 configured to detect contraband objects.

21. The system of claim 11 configured to perform medical diagnostics on a subject.

22. A method for x-ray scanning an object, comprising:

emitting a beam of electrons from an electron source to strike a discrete or swept focal spot on a target for creating x-rays from the discrete or swept focal spot;

focusing the beam of electrons from said electron source prior to said electron beam emissions striking said target;

detecting the x-rays created from the discrete or swept focal spots; and providing protection to said electron source from transient beam currents, material emissions from said target, and electric field transients.

23. The method of claim 22, further comprising selectively permitting and inhibiting generation of discrete or swept focal spots on said target.

24. The method of claim 22, further comprising enclosing said target within a first vacuum vessel and enclosing said electron source within a second vacuum vessel.

25. The method of claim 24, further comprising pumping said first and second vacuum vessels.

26. The method of claim 25, further comprising connecting said first and second vacuum vessels with a channel.

27. The method of claim 26, further comprising placing gate valves in said channel between said first and second vacuum vessels.

28. The method of claim 22, further comprising positioning said electron source within an alcove configured to inhibit damage to said electron source from a deflection of a beam of ions from the target toward said electron source.

* * * * *